United States Patent [19]

Percec et al.

[11] Patent Number: 4,806,617

[45] Date of Patent: Feb. 21, 1989

[54] POLY(DINAPHTHYL ARYLENE ETHER) AND PREPARATION THEREOF

[75] Inventors: Virgil Percec, Pepper Pike; Paul P. Nicholas, Broadview heights, both of Ohio

[73] Assignee: The B.F. Goodrich Company, Akron, Ohio

[21] Appl. No.: 25,544

[22] Filed: Mar. 13, 1987

[51] Int. Cl.$^4$ .............................................. C08G 65/00
[52] U.S. Cl. ...................................... 528/86; 528/125; 528/170; 528/171; 528/174; 528/210; 528/212; 528/214; 528/215; 528/217
[58] Field of Search ................. 528/86, 171, 125, 170, 528/210, 174, 212, 214, 215, 217

[56] References Cited

U.S. PATENT DOCUMENTS 3,810,870  5/1974  Feasey et al. ......................... 528/86

*Primary Examiner*—Harold D. Anderson

*Attorney, Agent, or Firm*—James R. Lindsay; Alfred D. Lobo

[57] ABSTRACT

When two 4-naphthoxyphenyl moieties are connected through a polar linking group, Y, it does not interfere with an oxidation process which results in dehydrogenative polymerization to yield polyarylene polyether (PAPE) polymers having a weight average mol wt greater than 10,000. Homo- and copolymers having a repeating unit in which a 4,4'-di(1-naphthoxyphenyl) moiety is connected through its phenyl rings to a bivalent polar residue are described. A specific monomer is selected from the group consisting of 4,4'-di(1-naphthoxy)diphenyl sulfone (DNDPS, Y=SO$_2$) and, 4,4'-di(1-naphthoxy)benzophenone (DNBP, Y=CO). Because the process provides thermoplastic PAPE polymers having a Tg in the range from about 250° C. to about 350° C. with excellent physical properties, the polymers are suitable for use in the fabrication of composites for aerospace vehicles subjected to elevated temperatures.

4 Claims, 1 Drawing Sheet

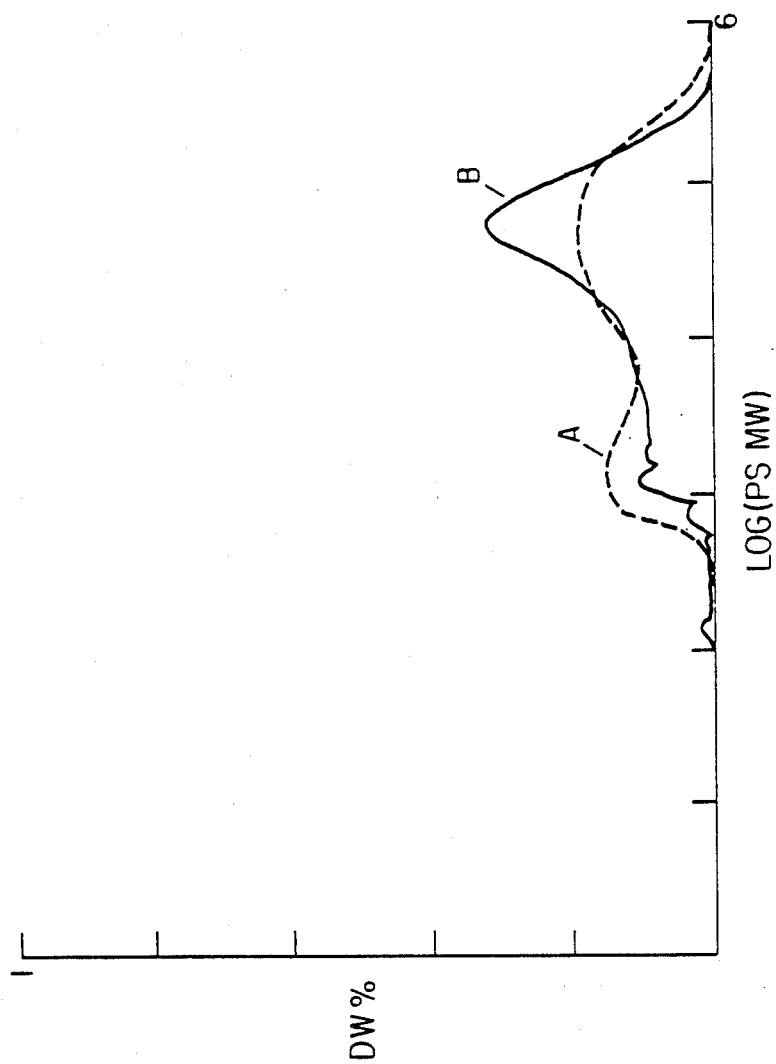

POLY(DINAPHTHYL ARYLENE ETHER) AND PREPARATION THEREOF

BACKGROUND OF THE INVENTION

High impact strength, high glass transition temperature (Tg), and resistance to thermal degradation, are among the most desirable properties of commercially successful high performance resins. Polymers of arylene ether ketones and arylene ether sulfones, referred to as polyarylene polyethers and polyarylene polythioethers, together referred to herein as polyarylene poly(thio)ethers (PAPE) such as those disclosed in U.S. Pat. No. 4,562,243, rank high among polymers which have such desirable properties, particularly excellent thermal properties and impact strength. The emphasis has been to produce other aromatic polyethers which have even better properties, and might be even more economical to manufacture. Of particular interest are thermoplastics of this kind having a Tg high enough for advanced aerospace applications, exceeding that obtainable with the aforesaid PAPE polymers. High Tg PAPE polymers would result from appropriate monomers containing fused aromatic rings, particularly if polymerization occurred through coupling of such rings. This invention describes the preparation of such polymers.

The polymers of this invention are prepared by the well known Scholl reaction which is generally applied to the dehydrogenative condensation of aromatic compounds to yield dimers, or other relatively small molecules. The dehydrogenative condensations (also referred to as "oxidative polymerization") can take place in either an inter- or an intramolecular way. Intermolecular Scholl reactions are numerous and include such reactions as the formation of biphenyl from benzene:

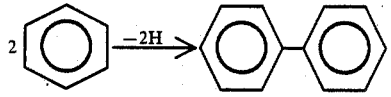

Both inter- and intramolecular dehydrogenation of aromatic nuclei proceed in the presence of oxidizing agents, the latter resulting in the formation of a condensed ring system. These condensations occur with oxidizing agents that can include certain transition metal salts, e.g. FeCl$_3$ or CuCl$_2$, or Lewis acid catalysts in oxidizing media, e.g. nitrobenzene.

The elimination of two aryl-bound hydrogens accompanied by the formation of an aryl-aryl bond under the influence of Friedel-Crafts catalysts is referred to as the Scholl reaction. (see "Friedel-Crafts and Related Reactions" by George Olah, vol II, Part 2, Chapter XXIII titled "Dehydrogenation Condensation of Aromatics (Scholl and Related Reactions)" by A. T. Balaban and C. D. Nenitzescu, Interscience Publishers 1964.

In an article titled "Studies of the Scholl Reaction: Oxidative Dehydrogenation involving 1-Ethoxynaphthalene and Related Compounds" by G. A. Clowes, J.Chem.Soc., C, 2519 (1968) the author reportedly obtained a very low molecular weight (mol wt) poly(binaphthylene oxide) from the oxidation of 1,1'-binaphthyl ether. In light of his results, it is perhaps to be expected that Clowes did not suggest the application of the Scholl reaction for the preparation of relatively high mol wt polymers by the polymerization of monomers containing aromatic rings.

But some time later, purportedly "high" mol wt linear poly(dinaphthyl alkylene ether) polymers of di(1-naphthoxy) alkanes were obtained by Feasey et al as disclosed in U.S. Pat. No. 3,810,870 and in an article titled "Preparation of poly(dinaphthyl alkylene ethers) by oxidative polyarylation and their crystallization behaviour". These polymers were derived, like that of Clowes, from either bis-(1-naphthyl)ether having the structure:

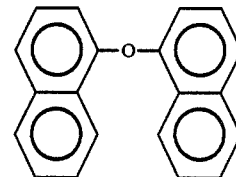

or from a di-1-naphthoxy alkane having the structure:

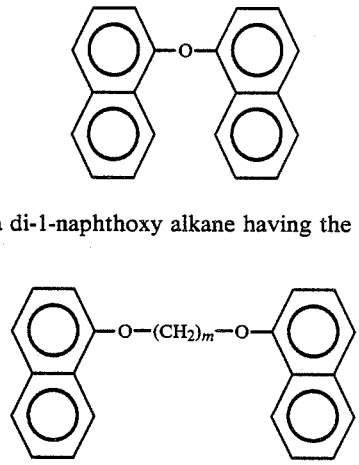

wherein m is an integer in the range from 1 to about 20, so that the repeating unit would have the following structure:

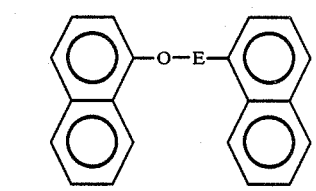

wherein E is a direct link or a group having the formula —X—O— where X is a bivalent non-polar residue.

Since Feasey et al teach away from the use of polar residues, one would expect that the particular non-polar linking of the naphthoxy moieties was essential to provide the purportedly high mol wt polymers which Clowes failed to produce without it. Note however, that there is no data, other than the reduced viscosity in the Table in col 4, to provide evidence of mol wt, and as one skilled in the art will appreciate, the reduced viscosity alone cannot define the mol wt of the polymer. Though a wide range of non-polar bivalent aromatic or aliphatic residues containing up to 20 carbon atoms, is listed, there is now reason to believe that Feasey's choice of non-polar residue may not have been as effective as it was hoped. The results of polymerization with a non-polar 2,2'-biphenylene residue specifically suggested by Feasey et al, which results are presented hereinbelow, indicate an unsatisfactory polymerization. It is one thing to expect the Scholl reaction to proceed without interfering chemical events when only two, three, or less than about 10 molecules are to be successively dehydrogenated thus forming a macromolecule; it is a wholly different matter to expect the reaction to so proceed unerringly over the course of condensing a hundred or more molecules into a long chain.

A recent review article by W. Koch, W. Risse and W. Heitz, *Makromol Chem* 184 779 (1983) surveys the polycondensation reactions in which radical-ions are considered responsible for chain propagation in polycondensation reactions, e.g. the synthesis of poly(2,6-dimethyl-1,4-phenylene oxide), poly(1,4-phenylene oxide), poly(1,4-phenylene sulfide), and poly(1,4-phenylene). In such reactions in which the mechanism is described by Heitz as a "reactive intermediate condensation", charge at the cationic end group can be delocalized through connected aromatic segments. To the extent that such delocalization applies to the polymerization of di(1-naphthoxy) monomers, then polar, electron withdrawing connecting groups could increase the oxidation potential, making oxidative polymer ization more difficult.

The formation of polymers having a large fraction with mol wt greater than about 10,000 is made even more difficult because the chains tend to undergo a ring closure, resulting in cyclic oligomers. Further, we have found that successful polymerizations can be temperature sensitive, resulting, for one specific example, in crosslinking at temperatures exceeding about 80° C. The formation of cyclic polymers and crosslinking can be sensitive to the particular character of the linking group, but the extent of such sensitivity for each polymer can only be determined by actual testing.

Particularly since the known requirement for the linking group was that it include a non-polar residue, there was no basis for reaching an informed conclusion that a linking residue containing a polar group might lend itself to a successful Scholl polymerization. There was no reason to explore the possibility that a di(4-naphthoxyphenyl) repeating unit linked with a polar residue, or a linking group containing a polar residue, might yield a polymer with desirable properties.

SUMMARY OF THE INVENTION

It has been discovered that when di(4-naphthoxyphenyl) moieties are connected through a polar linking group, it does not interfere with the oxidation process resulting in dehydrogenative polymerization to yield polyarylene polyether (PAPE) polymers having a weight average mol wt greater than 10,000.

It is therefore a general object of this invention to provide homo- and copolymers (1) having a repeating unit in which a 4,4'-di(1-naphthoxyphenyl) moiety is connected through its phenyl rings to a bivalent polar residue or moiety Y, thus:

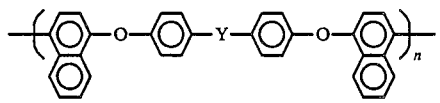
(1)

wherein, Y represents $SO_2$, C=O, S, O, $-[O-SiR_2-]_m-O$,

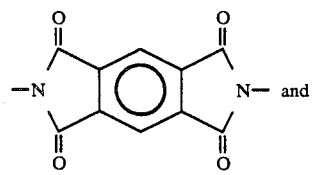 and

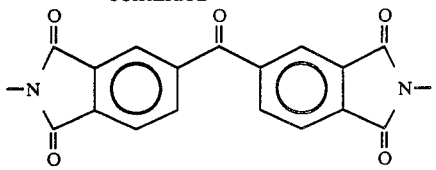

where
R represents $C_1-C_{12}$ alkyl, $C_6-C_{10}$ and $C_7-C_{18}$ aralkyl,
m is an integer in the range from 1 to about 20, and,
n is an integer in the range from 2 to about 500.

It is a specific object of this invention to provide a process for the preparation of thermoplastic PAPE polymers having a Tg above about 250° C. by utilizing a dehydrogenative condensation to polymerize a monomer (2)

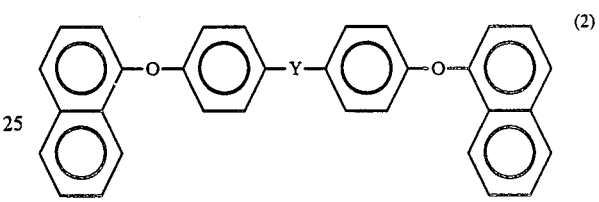
(2)

selected from the group consisting of 4,4'-di(1-naphthoxy)-diphenyl sulfone (DNDPS, $Y=SO_2$) and, 4,4'-di(1-naphthoxy)benzophenone (DNBP, Y=CO).

BRIEF DESCRIPTION OF THE DRAWING

The foregoing and other objects and advantages of our invention will appear more fully from the following description made in connection with the accompanying drawing, wherein is shown the differential weight per cent (DW %) plotted against log (molecular weight relative to polystyrene), log(PS MW) illustrating the bimodal distributions of two polymers and the relative molecular weight populations.

DETAILED DESCRIPTION OF PREFERRED EMBODIMENTS

Dehydrogenative condensation (or oxidative polymerization) of bis(naphthoxy) monomers produces rings competitively with linear chain extension, making it difficult to produce long chains. The etent to which long chains are formed is influenced by the linking or connecting group. A good example to illustrate the difference in the effects of the linking groups is the formation of the polymer from 2,2'-bis(1-naphthoxy)-biphenyl having the following repeating unit:

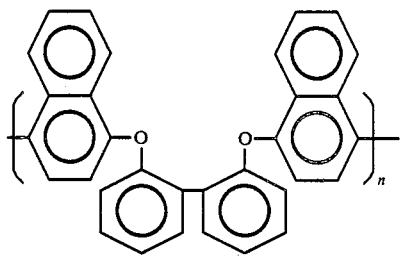

and, the polymer from 4,4'-di(1-naphthoxy)diphenyl sulfone (1) ($Y=SO_2$) or poly(DNDPS).

Referring to the figure there is shown a plot of logarithm of molecular weight (mw) relative to polystyrene, log(PS mw), against differential weight percent (DW %) made in accordance with ASTM test procedures D3536-76 and D3593-80, the disclosures of which are incorporated by reference thereto as if fully set forth herein. The plot is generated on a gel permeation chromatograph (GPC) so that the weight fraction of polymer havng a particular mol wt may be determined for each of the foregoing polymerizations.

Curve A (dashed line), is a plot for the polymer from 2,2'-bis(1-naphthoxy)biphenyl. It clearly shows two different mw populations separated by a valley in the curve. Considerable low mw polymer is present, with 37% of the total population being below 8,000. This is significant because the extent of ring formation is too great to be useful for making a high mol wt polymer economically. That this low mw fraction consists largely of cyclic oligomers is confirmed by size exclusion HPLC/mass spectrometry.

Curve B (solid line), is a plot for the polymer from 4,4'-di(1-naphthoxy)diphenyl sulfone, polymerized under the same conditions as those used for the foregoing 2,2'-bis(1-naphthoxy)biphenyl plotted as curve A. Curve B also shows a bimodal distribution but only a relatively small low mw population. The major portion of the polymer has a mw greater than 10,000 to about 200,000.

In addition to the difficulty of making polymer with a mw greater than 10,000, we find that the polymerization reaction can produce crosslinking which renders the crosslinked polymer insoluble even at high dilution. Crosslinking appears to originate from abnormal coupling of a growing chain end with one of the carbon atoms in another chain. The extent to which the connecting group influences crosslinking can only be determined by actual testing.

The extent of crosslinking as influenced by reaction temperature is demonstrated by a comparison of the reactions carried out at 30° C. and 90° C. respectively.

EXAMPLE 1

The following ingredients are used in the polymerization of DNDPS:

| | |
|---|---|
| DNDPS | 5.00 g (0.00995 mol) |
| FeCl3 (anhydrous) | 5.24 g (0.0323 mol) |
| nitrobenzene | 40 ml (for FeCl3) |
| | 20 ml (for monomer) |

The DNDPS was charged into a 100 ml glass vessel prepared from a 45/50 female glass joint. The head was prepared from the corresponding male joint and contains smaller joints for a paddle stirrer, thermowell, nitrogen inlet, and an additional funnel fitted with a gas bubbler. The flask was charged with monomer and nitrobenzene, vigorously stirred and equilibrated in a constant temperature bath. The system was purged with nitrogen and the ferric chloride solution delivered over a 3 min period. After stirring for 17 hr, the system was cooled and the reaction mixture added to 500 ml of rapidly stirred methanol. The larger of solid pieces of polymer formed were cut into smaller pieces and the solids resuspended in fresh methanol overnight. It was then filtered, and dried in a vacuum oven at 85° C. The polymerizations carried out at 30√ C. and 90° C. gave 96 and 100% yields respectively. Both were cryogenically ground to a fine powder, and 3 g of each was vigorously stirred with chloroform for 24 hr. The volume of chloroform used was 45 ml for the polymer prepared at 30° C., and 100 ml for the polymer prepared at 90° C. While 85% of the former was soluble, only 29% of the latter dissolved.

In a preferred embodiment of our invention, the monomer (2) is prepared by the displacement of halide, X, from the 4,4'-dihalophenyl end groups in the structure (3)

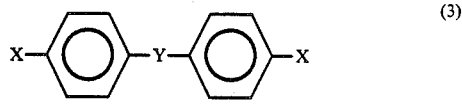

(3)

wherein Y is a divalent, electron withdrawing group which activates the halogens toward displacement, with the postassium salt of 1-naphthol. Most preferred are $SO_2$ and $C=O$. Both X=F and Cl are suitable, F for its high reactivity and Cl for its low cost.

In those cases where the connecting group, Y, does not provide sufficient activation toward displacement, other routes are required. For example, when Y=OSi-(CH3)2O, 4-)1-naphthoxy)phenol is coupled with dimethyldichlorosilane, and when Y is one of the phthalimide residues shown hereinabove, 4,4'-di[4-aminophenoxy-1-naphthyl](4)

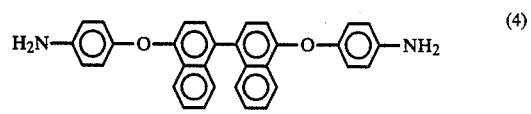

(4)

is first partially condensed to the polyamic acid of the corresponding dianhydride. Evaporation of solvent followed by thermal condensation gives the phthalimides shown.

The polymerization rate of the monomers is controlled by the amount and rate of addition of ferric chloride or other oxidant used, the stirring intensity of the polymerizing reaction mass, and reaction temperature. Other process variables can be, and may need to be varied depending upon the selection of Y.

Since the rate of polymerization is very high, it is preferred to add the catalyst slowly, with rapid stirring, or low mw polymer will result. Less than a stoichiometric amount of $FeCl_3$ to monomer produces polymer having a weight average mol wt $\overline{Mw}$ lower than 10,000, independent of the overall concentration of the monomer. Preferred mole ratios of oxidant to monomer is in the range from about 2:1 to about 8:1, most preferred being about 4:1.

The polyether sulfones obtained from DNDPS and the polyether ketones obtained from DNBP are each soluble in conventional solvents such as chloroform and methylene chloride. They do not lose weight up to about 400° C. (TGA) and have high Tgs in the range from about 250° C. to about 300° C., which is higher than that for PAPE polymers produced by nucleophilic displacement, as taught in U.S. Pat. Nos. 4,562,243; 4,634,742; and, 4,638,039.

EXAMPLE 2

Synthesis of 4,4'-di(1-naphthoxy)diphenyl sulfone (DNDPS) having the structure 92) wherein Y=SO2:

A 2-liter, 3-necked flask equipped with a thermometer, nitrogen inlet, Dean-Stark trap, and condenser was charged with (0.692 mol) of 1-naphthol, 51.4 g (0.796 mol) of 87% KOH, 20 ml water, and 1 liter of dimethylsulfoxide (DMSO). The stirred mixture was refluxed under nitrogen to remove water azeotropically. The mixture was cooled to 90° C., and 94.6 g (0.328 mol) of 4,4'-dichlorodiphenylsulfone (DCDPS) added. The mixture was reheated to 150°–155° C. as toluene was removed by distillation and maintained at that temperature for 6 hr. The mixture was then cooled to about room temperature, poured into 5 liters of stirred methanol containing 1 liter of water, filtered, and dried in a vacuum oven. The combined product from two such preparations was dissolved in toluene and passed through 200 g of Woelm N alumina. The solution was then heated to 70° C. and hexane added until turbid. Cooling, finally in ice, gave the main crop of crystals. A second crop was obtained similarly, giving 277 g (0.556 mol), a yield of 85% having a melting point 154° C.

The above structure was confirmed by $^1$H-NMR spectrographic analysis.

EXAMPLE 3

Synhesis of poly(DNDPS) having the structure (1) wherein Y=SO$_2$:

A 2-liter creased resin flask was fitted with a glass cover containing ports for nitrogen, an addition funnel fitted with a gas bubbler, and a Teflon propeller stirrer. The flask was charged with 110 g (0.219 mol) of 4,4'-di-(1-naphthoxy)diphenyl sulfone (DNDPS) and purged with nitrogen. Nitrobenzene (440 ml) dried over 3A molecular sieves, was added. A solution of 115.3 g (0.7106 mol) of anhydrous FeCl$_3$ was dissolved in 880 ml of dried nitrobenzene and charged to the addition funnel. The flask was thermally equilibrated at 30° C. while vigorously stirred. The FeCl$_3$ solution was added over a period of 43 min. Polymer precipitated during 17 hr of stirring. The nitgobenzene solution was decanted off and the polymer subdivided and stirred with 1 liter of chloroform containing 250 ml of water. The chloroform layer was separated, washed with additional water, and filtered under pressure. The filtrate was then precipitated from methanol using a draft tube. After filtering and drying in a vacuum oven at 125° C., 79.4 g of polymer was obtained. Precipitation of the nitrobenzene-soluble polymer gave an additional 9.5 g for a combined yield of 81%. The nitrobenzene insoluble polymer had Tg 284° C., Mw 68,700, Mn 11,900, peak 59,000 (polystyrene equivalents).

The structures of the foregoing polymer was confirmed by $^1$H-NMR spectrographic analysis.

EXAMPLE 4

Synthesis of 4,4'-di(1-naphthoxy)benzophenone (DNBP) having the structure (2) wherein Y=CO:

DNBP was prepared by the etherification of 20 g (91.66 mmole) of 4,4'-difluorobenzophenone with 33.04 g (229.15 mmole) of 1-naphthol in the presence of 34.83 g (252.06 mmole) of K$_2$CO$_3$ in dimethylacetamide under reaction conditions generally analogous to those set forth hereinabove for synthesis of DNDPS. The product was crystallized from ¼, v/v acetone/methanol and has m p 108.8° C. The yield was 91%. The above structure was confirmed by $^1$H-NMR spectrographic analysis.

EXAMPLE 5

Synthesis of poly(DNBP) having structure (1) wherein Y=CO:

The polymerization of DNBP is carried out in a manner analogous to that described hereinabove for DNDPS, and the polymer obtained purified by conventional methods.

The structure of the polymer was confirmed by $^1$H-NMR spectrographic analysis.

EXAMPLE 6

Synthesis of bis[N-(4-naphthoxyphenyl(]imide of 1,2,4,5-benzenetetracarboxylic dianhydride ("BNIB") having the structure (2) wherein

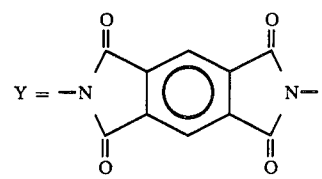

This imide monomer, BNIB, is prepared by the procedure described by Bell, V. L. et al in *J. Poly. Sci., Part A.* 24, 2647 (1986) by the following reaction:

A 500 ml, three-necked flask was fitted with an addition funnel, paddle stirrer, and thermometer. The flask was charged with 20.9 g (0.096 mol) of BNIB and 200 ml of dimethyl formamide (DMF). The mixture was stirred until a solution was developed. The amine (45.0 g, 0.192 mol), dissolved in 50 ml of DMF was placed in the addition funnel, and added to the stirred anhydride solution (mild exotherm). After 30 min, acetic anhydride (24.5 g, 0.24 mol) and sodium acetate (1.92 g) were added. The mixture was heated to 50° C. Solid began to separate from solution. After 2 hr at 50° C. the mixture was added to 1 liter of rapidly stirred water. The mixture was filtered, washed with water, and dried in a vacuum oven overnight at 60° C. Obtained 55.2 g (0.0846 mol) of yellow solid in 88% yield, m.p. above 300° C.

The monomer is insoluble. The corresponding polymer is therefore prepared by a different route described by Bell, V. L. et al in J. Polym. Sci., Polym. Chem. Ed. 14, 2275 (1976).

EXAMPLE 6

Synthesis of polyimide, "poly(BNIB)" having structure (1) wherein

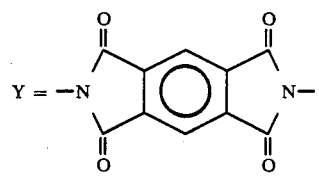

A 100 ml, three-necked flask equipped with a nitrogen inlet, gas bubbler, and magnetic stirrer bar was purged with nitrogen and charged with 50 ml of dry dimethylacetamide containing 3.00 g (6.40 mmols) of 4,4]-di[4-aminophenoxy-1-naphthyl]. To the stirred solution was added 1.40 g (6.40 mmols) of BNIB. The solution was stirred for 24 hr at room temperature.

Polymer films are obtained by casting the solution on glass plates and drying in air followed by further drying

EXAMPLE 7

Synthesis of polyimide having the structure (1) wherein

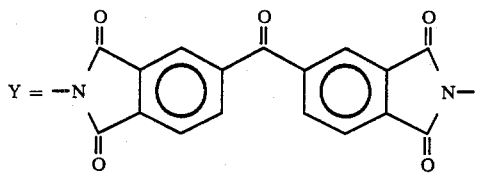

The polymer is prepared in a manner analogous to that described hereinabove in Example 6, employing 2.06 q of 3,3',4,4'-benzophenone tetracarboxylic dianhydride, casting on a glass plate, and drying in an air oven at temperature stages ending at 300° C.

EXAMPLE 8

Synthesis of silanated polyethers having the structure (1) wherein $Y=-[O-Si(CH_3)_2-O]-$ A 500 ml, three-necked flask was fitted with a magnetic stirrer, nitrogen inlet, and a Dean-Stark trap with a gas bubbler mounted on the water cooled condenser. The flask was charged with 60.0 g (0.254 mol) of 4-(1-naphthoxy)phenol and 300 ml of toluene. The solution was stirred under nitrogen while water was rigorously removed by azeotropic distillation. The solution was cooled and 0.127 mol of dimethyldichlorosilane was slowly added. HCl was purged from the system. The monomer was recovered by concentrating the solution on a rotary evaporator at 80° C., and the product allowed to crystallize on cooling.

The monomer is polymerized in a manner analogous to that described in Example 2 hereinabove.

EXAMPLE 9

In a manner analogous to that described in Example 8 hereinabove, 0.127 mol of 1,3-dichlorotetramethyldisiloxane was slowly added to the 4(1-naphthoxy)-phenol. The product obtained is the monomer (2) wherein $Y=-[O-Si-(CH_3)_2]_2-O-$

EXAMPLE 10

Synthesis of copolymer of DNDPS and DNBP:

A mixture comprising 55 g (0.110 mol) of DNDPS (1), $Y=SO_2$, and 51.3 g (0.110 mol) of DNBP (1), $Y=CO$, were copolymerized and isolated in a manner analogous to that described in example 2 hereinabove.

The structure of the polymer was confirmed by $^1H$-NMR spectrographic analysis.

Details of polymerization conditions and characterization of the poly(DNDPS) and poly(DNBP) formed at room temperature in nitrobenzene, using a very small quantity of monomer (1.0 g), are summarized in Tables 1 and 2 respectively, herebelow.

TABLE I

Synthesis and Characterization of Poly(DNDPS). Room temperature polymerization in nitrobenzene; 1.0 g of DNDPS; reaction time 4 hrs

| No. | FeCl₃/DNDPS mole ratio | Solvent ml/g of DNDPS | ml/g of FeCl₃ | Yield % | $\overline{Mn}$ GPC | $\overline{Mw}$ | $\overline{Mw}/\overline{Mn}$ | Tg (°C.) |
|---|---|---|---|---|---|---|---|---|
| 1 | 2 | 6 | 4.66 | 63 | 2879 | 8936 | 3.10 | 242.5 |
| 2 | 4 | 6 | 7.76 | 70 | 9897 | 25808 | 2.60 | 262.8 |
| 3 | 4 | 5 | 7.76 | 75 | 12942 | 34518 | 2.66 | 271.8 |
| 4 | 4 | 4 | 7.76 | 70 | 15119 | 31012 | 2.05 | 274.9 |
| 5 | 4 | 4 | 7.76 | 75 | 16176 | 49942 | 3.08 | 270.0 |
| 6 | 4 | 3 | 7.76 | 70 | 18221 | 70121 | 3.85 | 270.0 |
| 7 | 4 | 2[B] | 6.20 | 73 | 20569 | 152469 | 7.40 | 280.7 |
| 8 | 4 | 2 | 7.76 | 70 | 22734 | 87496 | 3.85 | 275.6 |
| 9 | 4 | 2[C] | 6.20 | 80 | 24392 | 40023 | 1.64 | 273.1 |
| 10 | 4 | 2[D] | 6.20 | 80 | 32103 | 64225 | 2.00 | 276.6 |
| 11 | 4 | 2 | 6.20 | 83 | 59015 | 98240 | 1.66 | 277.5 |
| 12 | Cyclics[A] | — | — | — | 1294 | 1540 | 1.19 | 253.2 |

[A]cyclics from sample 11, isolated by precipitating the chloroform solution of polymer into acetone
[B,C & D]:3 ml, 4 ml, & 2 ml, respectively of nitrobenzene were added 15 min after FeCl₃ solution was added

TABLE II

Synthesis and characterization of Poly(DNBP). Room temperature polymerization in nitrobenzene; 1.0 g of DNBP[A]

| No. | Solvent ml/g of DNBP | ml/g of FeCl₃ | Reaction time, hr. | Yield % | $\overline{Mn}$ GPC | $\overline{Mw}$ | $\overline{Mw}/\overline{Mn}$ | Tg (°C.) |
|---|---|---|---|---|---|---|---|---|
| 1 | 3.0 | 7.2 | 4.0 | 67 | 4997 | 29029 | 4.6 | 213.8 |
| 2 | 2.0 | 7.2 | 4.0 | 70 | 9760 | 31093 | 3.2 | 227.7 |
| 3 | 1.5 | 5.75 | 1.5 | 73 | 21280 | 94506 | 4.4 | 251.1 |
| 4 | 1.5 | 5.39 | 1.5 | 81 | 38006 | 111178 | 3.8 | 249.0 |
| 5 | Cyclics[B] | — | — | — | 1261 | 3546 | 2.8 | 197.7 |

[A]FeCl₃/DNBP mole ratio = 4.0
[B]Cyclics from sample No. 3 isolated by precipitating the chloroform solution of polymer into acetone

We claim:

1. A substantially linear thermoplastic polyarylene polyether polymer having a repeating unit represented by the structure:

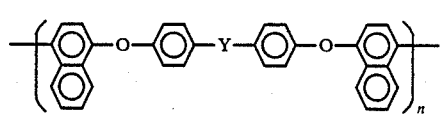

wherein, Y represents a divalent connecting radical selected from the group consisting of $SO_2$, $C=O$,

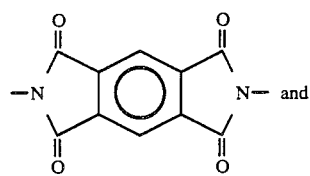

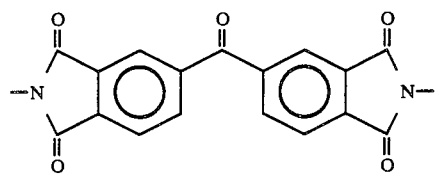

R represents $C_1$–$C_{12}$ alkyl, $C_6$–$C_{10}$ aryl or $C_7$–$C_{18}$ aralkyl, and, n is an integer in the range from above 2 to abut 500, the polymer having a minimum Tg of about 200° C. and a weight average molecular weight Mw in the range from about 10,000 to about 200,000.

2. The polymer of claim 1 wherein Y is $SO_2$.

3. The polymer of claim 1 wherein Y is C=O.

4. A thermoformed shaped article of a substantially linear thermoplastic polyarylene polyether (PAPE) having a repeating unit represented by the structure:

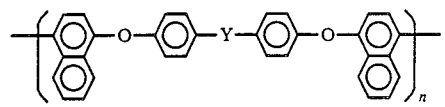

wherein, Y represents a divalent connecting radical selected from the group consisting of $SO_2$, C=O,

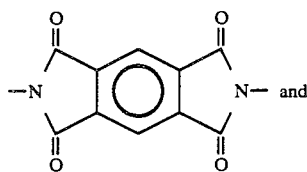

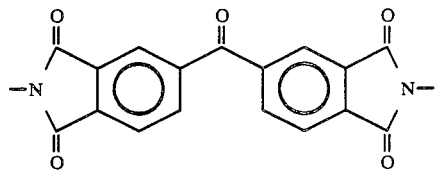

R represents $C_1$–$C_{12}$ alkyl, $C_6$–$C_{10}$ aryl or $C_7$–$C_{18}$ aralkyl, and, n is an integer in the range from 2 to about 500, said PAPE having a weight average molecular weight Mw in the range from above about 10,000 to about 200,000, and, a Tg in the range from about about 200° C. to about 350° C.

* * * * *